United States Patent [19]

Saxena et al.

[11] Patent Number: 4,966,888

[45] Date of Patent: Oct. 30, 1990

[54] HCG-HLH RECEPTOR AND HCG-HLH RECEPTOR-HCG COMPLEX AS ANTIGENS, ANTIBODIES THERETO AND CONTRACEPTIVE VACCINE

[75] Inventors: Brij B. Saxena, Englewood; Premila Rathnam, Englewood Cliffs, both of N.J.; Mukul Singh, New York, N.Y.

[73] Assignee: Cornell Research Foundation, Inc., Ithaca, N.Y.

[21] Appl. No.: 910,554

[22] Filed: Sep. 23, 1986

Related U.S. Application Data

[63] Continuation of Ser. No. 752,497, Jul. 8, 1985, abandoned, which is a continuation of Ser. No. 446,145, Dec. 2, 1982, abandoned.

[51] Int. Cl.$^5$ .................. A61K 37/00; A61K 37/38; A61K 37/29; A61K 37/36
[52] U.S. Cl. ........................ 514/2; 530/398; 530/399; 530/350; 435/70.1; 435/70.3; 514/8; 514/12; 424/88
[58] Field of Search ............... 435/68, 70, 70.1, 70.3; 530/313, 397, 398, 399, 812, 851, 833, 834, 853, 350; 514/2, 8; 424/88

[56] References Cited

U.S. PATENT DOCUMENTS

| | | | |
|---|---|---|---|
| 4,016,250 | 4/1977 | Saxena | 530/398 |
| 4,161,519 | 7/1979 | Talwar | 424/88 |
| 4,310,455 | 1/1982 | Bahl | 530/350 |
| 4,560,649 | 12/1985 | Satena et al. | 435/7 |

OTHER PUBLICATIONS

Satena, Brij, *Methods Mol. Biol.*, vol. 9, pt. 1, pp. 251-299, 1976 (see pp. 275-280 especially).

*Primary Examiner*—Robin L. Teskin
*Attorney, Agent, or Firm*—Sughrue, Mion, Zinn Macpeak & Seas

[57] ABSTRACT

Purified hCG-hLH receptor, hCG-hLH receptor-hCG complex and combinations between their subunits as antigens, as well as antibodies thereto which are useful as a contraceptive vaccine.

32 Claims, 6 Drawing Sheets

HCG-HLH RECEPTOR AND HCG-HLH RECEPTOR-HCG COMPLEX AS ANTIGENS, ANTIBODIES THERETO AND CONTRACEPTIVE VACCINE

The invention herein was made in the course of work under one or more grants from the U.S. Department of Health and Human Resources.

CROSS-REFERENCE TO RELATED APPLICATIONS

This application is a continuation-in-part of Ser. No. 752,497, filed July 8, 1985 now abandoned which is a continuation of Ser. No. 446,145, filed Dec. 2, 1982, now abandoned.

FIELD OF THE INVENTION

The present invention relates to purified hCG-hLH receptor, hCG-hLH receptor-hCG complex and combinations between their subunits as antigens, as well as antibodies thereto which are useful as a contraceptive vaccine.

BACKGROUND OF THE INVENTION

In recent years significant effort has been expended toward developing an immunological approach to contraception. The basic approach has been to either provide an antibody (passive immunization), or to elicit an antibody response (active immunization), to a hormone critical to the establishment and/or maintenance of pregnancy. The production and effects of human chorionic gonadotropin (hCG) in pregnancy have singled out hCG as a prime candidate for studies in immunological contraception. hCG is not present in the normal, healthy female prior to fertilization, but is secreted by the developing blastocyst and can be detected in pregnant women as early as 6 to 7 days after fertilization. hCG, in turn, initially acts upon the corpus luteum, and later upon the placenta, in causing each of them to secrete progesterone. Progesterone, at a high level, acts upon the endometrium to aid in preparing it for implantation and to maintain it after implantation. Therefore, both hCG and progesterone are essential for pregnancy to proceed immediately following fertilization. However, a significant reduction of hCG level prevents sufficient hCG from interacting with the hCG receptors of the corpus luteum and the placenta for maintenance of the high level of progesterone required for pregnancy. Progesterone drops back to or remains at a level too low for support of the endometrium, in the absence of hCG.

A number of researchers have attempted to develop contraceptive vaccines which immunologically block progesterone production. These vaccines provide or produce hCG antibodies to immunologically interact with circulating hCG determinants, thereby preventing the hCG determinants from reaching the hCG receptors of the corpus luteum and of the placenta.

Various problems have prevented commercialization of an hCG vaccine. First, hCG is a human hormone and humans will not normally produce antibody to a human hormone. This problem has been attacked by linking the hCG to a protein such as a hapten. Of course, the hCG antibodies can be produced in normal fashion in animals such as rabbits. However, problems still occur due to the non-specificity of hCG antibody, i.e., high levels of hCG antibody cross react with human luteinizing hormone (hLH); high levels of hCG antibody tend to cause abortion: etc. Low levels of hCG antibodies, which would not cross react with hLH, i.e., are hCG-β specific, were thought to offer the best chance of success, but in practice the circulating life of hCG is extended by formation of loose antigen-antibody complexes.

hCG and hLH, which share common receptors in the gonads as well as follicle stimulatory hormone (FSH), play important roles in the growth of ovarian follicles and in spermatogenesis in the testes.

A group of patents by Bahl (U.S. Pat. No. 4,310,455 and others) concern modification of the β subunit of hCG to produce a more specific hCG antigen for a variety of uses, including a contraceptive vaccine.

U.S. Pat. No. 4,161,519 by Talwar discloses a contraceptive vaccine comprising a purified β subunit of hCG conjugated to an antigen carrier.

A number of papers related to the general subject of contraception based on tying-up circulating hCG are found in *Recent Advances in Reproduction and Regulation of Fertility*, Elsevier/North Holland, 1977 (G. P. Talwar, Editor), pages 427–485.

SUMMARY OF THE INVENTION

Therefore, it is an object of the present invention to provide an improved contraceptive vaccine.

A more specific object of this invention is to provide a contraceptive vaccine which functions by preventing hCG from stimulating progesterone production of the corpus luteum and/or placenta.

Still another object of the present invention is to provide a contraceptive vaccine which overcomes the problems encountered with only hCG-based vaccines of the prior art.

A further object of the present invention is to provide contraceptive vaccines which can be used for either passive or active immunization.

Since hCG and hLH have common receptors an additional object of the present prevention is to use hCG-hLH receptor as an antigen and antibodies thereto in order to reversibly retard ovarian follicular growth and corpus luteum function which is believed to prevent ovulation and thus fertility.

Other objects of the invention, such as the provision of novel antigens and antibodies and methods to obtain such, will be apparent to the skilled artisan from the Detailed Description of the Invention, hereinbelow.

In accordance with the present invention, there is provided a contraceptive vaccine based on hCG, or a derivative: fragment or subunit thereof, and the common receptor for hLH and hCG, or a derivative, fragment or subunit thereof. In preferred embodiments of the invention, a dual purpose antigen is formed by complexing or conjugating the hCG-β subunit, or a derivative or fragment thereof, to the common biological receptor for hCG and hLH, or a derivative, fragment or subunit thereof. In active immunization embodiments, the two antigen components used in the present invention are administered either separately or in the form of the above-described complex or conjugate. In passive immunization embodiments, the antigen materials, separately or as the conjugate, are administered to a lower animal for production of antibodies, which are collected in the usual fashion and administered as a vaccine. In the most preferred embodiments of the present invention, only the common receptor for hLH and hCG, or a derivative, fragment or subunit thereof, is employed for either active or passive immunization as well as for the production of monoclonal antibodies for use as contraceptive agents.

As noted above, in the preferred embodiments of the invention, hCG-β is linked or complexed with the biological receptor for hCG and hLH (hereinafter "receptor") to form an antigen hCG-receptor unit capable of circulation in the bloodstream as an integral moiety. As disclosed herein, either the antigen hCG-receptor unit can be administered as a contraceptive vaccine as in the preferred embodiment of the invention or the antigen receptor only can be administered as a contraceptive vaccine as in the most preferred embodiment of the present invention, or in another embodiment at this time, antibody to either the hCG-receptor antigen or the receptor antigen can be administered as the contraceptive vaccine.

The common receptor for hLH and hCG is antigenic, so that the antibodies produced in response to the hCG-receptor unit contain determinants for both hCG and the receptor. In this manner, some of the antibodies of this invention not only interact with hCG to prevent hCG from reaching the receptors of the corpus luteum and placenta, but also blocks the receptor sites, thereby preventing any remaining unbound hCG from reaching the receptor sites.

In preferred embodiments of the invention, the hCG antigen consists essentially of the hCG-β subunit, or a derivative or fragment thereof, intact or modified.

In other preferred embodiments of the invention, the antibodies of the invention contain essentially monospecific determinants for the hCG-β subunit and essentially monospecific determinants for the receptor.

In passive immunization of the present invention, bifunctional and/or mono-functional polyclonal or monoclonal antibodies may be involved as well as idiotypic antibodies.

DETAILED DESCRIPTION OF THE INVENTION

Figure 1:
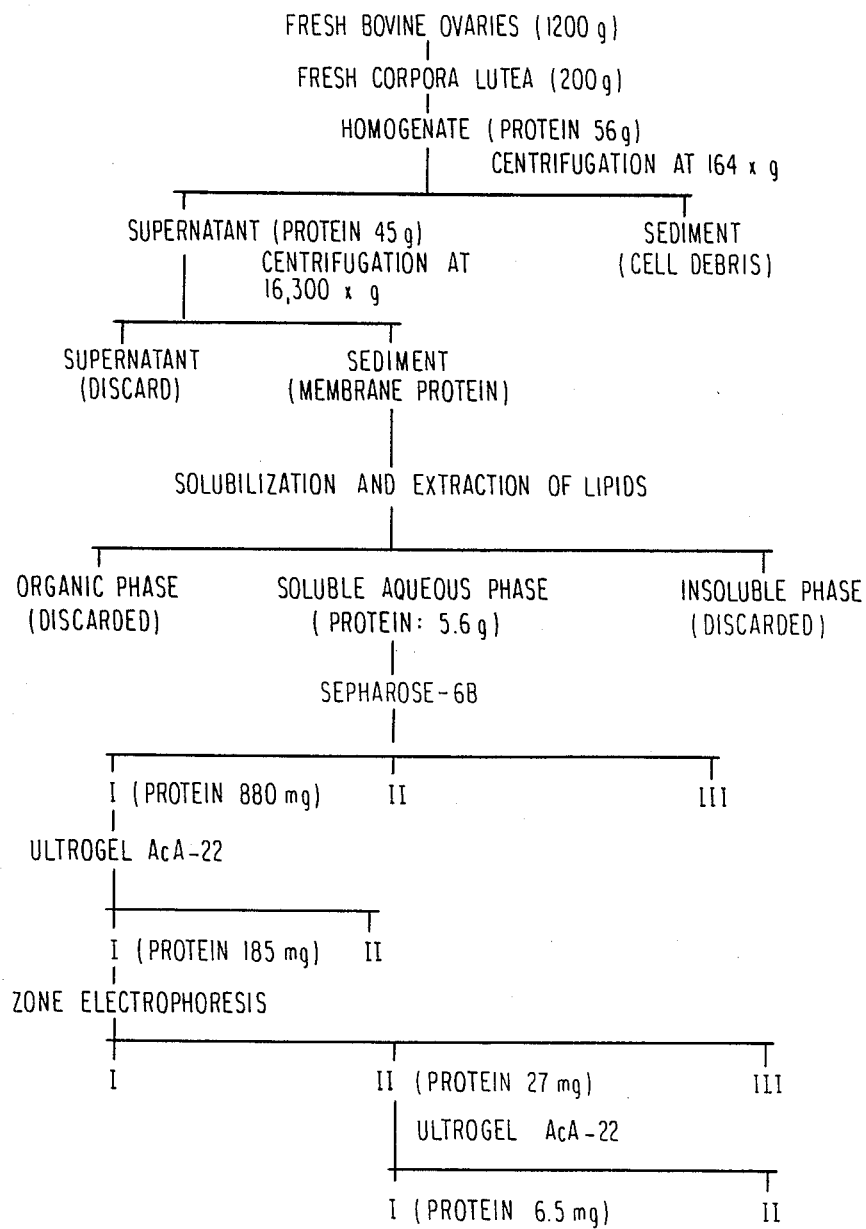
FIG. 1 is a flow diagram of the most preferred receptor purification method of the present invention which is described in Reference Example 2.

The concept underlying the present invention is the provision of antibodies (1) capable of blocking the determinant(s) of hCG which interact with the sites of the biological receptor for hCG, and/or (2) capable of interacting with said receptor sites. Therefore, (1) the determinants of hCG normally available for interaction with receptor sites are tied-up by antibody and/or (2) the sites of the receptor normally available for receiving hCG are blocked by antibody being associated therewith. The dual function of some of the antibodies used herein should provide effective contraception with relatively low antibody titers which is a key concept of this invention.

Although it is possible to utilize two separate antigens in the preferred embodiment of this invention, namely hCG (preferably hCG-β) and receptor, it is preferred to use a bifunctional antigen formed by linking or associating hCG with its receptor. Thus, one key reagent of the present invention is the common receptor for hLH and hCG.

The present inventors have previously isolated essentially pure receptor from naturally-occurring sources. Much of this work is described in application Ser. No. 311,736, filed Oct. 15, 1981, now abandoned, and the continuation-in-part application thereof, application Ser. No. 440,477, filed Nov. 9, 1982, now U.S. Pat. No. 4,560,649, both of which are incorporated herein by reference in their entirety.

It is preferred to use as the receptor antigen component herein, a relatively pure receptor fraction or sub-unit thereof, such as the electrophoretically homogeneous receptor and/or subunits thereof described in said U.S. Pat. No. 4,560,649. It is most preferable to use as the receptor antigen component herein a relatively pure receptor fraction or a subunit thereof as described in Reference Example 2 below. However, less pure receptor fractions, such as those disclosed in Saxena patents U.S. Pat. No. 4,016,250 and U.S. Pat. No. 4,094,963 and/or obtained from steps prior to the electrophoresis step of the purification processes of said co-pending Saxena et al applications, could be considered for use, but it is expected that superior results will be obtained with the purified receptor fractions. A substantially pure receptor fraction is preferred to reduce production of non-specific antibody.

The present inventors anticipate future modified forms of the receptor once additional analytical work is carried out on their electrophoretic homogeneous fraction, such as amino acid sequencing and analysis of the receptor and/or its oligomeric forms. Naturally, such a modified product of the receptor will be very useful in the practice of the present invention. Hereinbelow, there are set forth procedures for obtaining a purified receptor product and characterization of the electrophoretically pure receptor fraction.

REFERENCE EXAMPLE 1: RECEPTOR PURIFICATION 1200 bovine ovaries stored at −60° C, were thawed. The Corpora lutea therefrom were homogenized for 15 to 20 seconds in 0.1 M Tris-HCl buffer (pH 7.4, containing 1 mM each of $CaCl_2$, $MgCl_2$ and dithiothreitol, 0.01% sodium azide, $10^{-6}M$ phenymethylsulfonyl fluoride) and 100 μg/ml soya bean trypsin inhibitor containing 15% sucrose in a tissue to buffer ratio of 1:10 (w/v). The homogenate was centrifuged for 30 minutes in 8 one liter capacity swing-out buckets at 1000 rpm (Sorvall, Newton, Conn.). The supernatant was recentrifuged at 7,000×g for 45 minutes. The yield was 100 grams of protein. The 7,000×g supernatant was concentrated 8-fold by an Amicon DC-10 unit equipped with HI-50 hollow fiber cartridge (Amicon, Lexington, Mass.) suspended in an equal volume of the Tris-HCl buffer, reconcentrated to the original volume to reduce sucrose concentration and stored in 200 ml aliquots at −60° C. (All temperature values herein are centigrade unless stated otherwise.) The yield at this stage was 77 grams of protein. This concentrate can be diluted with buffer and reconcentrated.

Next, the above obtained concentrated supernatant was fractionated by a linear sucrose density gradient centrifugation. This was accomplished by preparative fractionation of aliquots of 200 ml each (20 g protein) of the concentrated 7,000×g supernatant in a Beckman Model L2-65B refrigerated ultracentrifuge, using a 1.6 liter capacity rotor (Ti-50). A linear sucrose gradient from 35% to 10% was prepared by the aid of a Beckman gradient pump (Model No. 141). The sample was layered on top of the sucrose gradient, the rotor was accelerated to 30,000 rpm and the centrifugation was continued for two hours. The rotor was then decelerated to maintain 3,500 rpm. The sucrose density gradient was eluted by displacement with a 40% sucrose solution and 20 ml fractions were collected every 0.5 minute. Fractions were analyzed for specific binding by $^{125}$I-hCG. Two fractions eluted between 18 to 28% sucrose contained nearly all of the active receptor. Sucrose concentration was measured by refractive index. The obtained fractions totaled 6.2 g protein.

Thereafter, the two fractions were separately concentrated by an Amicon DC-2 unit equipped with a HI-50 cartridge. Then, the samples were diluted with the Tris-HCl buffer and re-concentrated in the same apparatus. Finally, this phase of the purification process was completed by centrifuging at 55,000 rpm for 4 hours to sediment the receptor protein. Percent recoveries for the two fractions were 60% and 92%, respectively. The sediments are combined at this point. The 10 mM Tris-HCl buffer (pH 7.2, containing 0.5% Triton X-100) was added to the receptor fraction (25 mg protein per ml), 1% Triton X-100 solubilized more protein but significantly reduced hormone binding activity, perhaps due to formation of Triton X-100 micelles. The suspension was sonicated at 50 watts, four times for 5 second duration each time at 4° C. to increase receptor protein solubilization and recovery of hormone-binding activity. The neutral lipids were extracted by shaking with an equal volume of chilled petroleum ether at 4° C. for one hr and finally centrifuging at 10,000 rpm for one hr. The organic solvent, the aqueous phase, and the insoluble residue were separated. The aqueous phase contained the solubilized receptor.

The aqueous layer was recentrifuged at 5 000 rpm and 943 mg of protein recovered. This product was purified by gel filtration on a column of Sepharose-6B. The column was eluted with the Tris-HCl buffer (pH 7.2, containing 0.5% Triton X-100) at a flow rate of 13.5 ml per hour. Six ml fractions were collected and tested for receptor using $^{125}$I-hCG, the fractions having significant receptor activity were pooled and then fractionated on multiple 2.8×35 cm columns of Sepharose-4B. It was found that the ascending chromatography on Sepharose-6B separated a large amount of the adenylate cyclase activity (retarded protein fraction) from the hormone binding activity (unretarded protein fraction). The sample at this point contained 22 mg protein per ml of the Tris-HCl buffer. Column elution was carried out using the Tris-HCl buffer (pH 7.2, containing 0.5% Triton X-100) at a flow rate of 8 ml per hour, 4 ml fractions were collected. In essence, the fraction obtained from the Sepharose-6B column was sub-divided into two fractions by the Sepharose-4B columns, one fraction containing most of the hormone binding activity (unretarded protein fraction) and the other fraction containing most of the 5' -nucleotidase activity (retarded fraction). Again, through testing by specific binding to $^{125}$I-hCG, the active fractions were pooled. The active fractions from four Sepharose-4B columns were concentrated 5-fold by an Amicon ultrafilter and gel-filtered through a 5×50 cm column of Ultrogel AcA-34 (LKB Instruments).

The Ultrogel AcA-34 column was eluted with 0.3 M lithium borate buffer (pH 7.2, containing 1 mM MgCl$_2$, 0.01% NaN$_3$ and 0.5% Triton) at a flow rate of 10ml/hr. 4 ml fractions were collected. The Ultrogel AcA-34 significantly reduced the Triton X-100 concentration to about 0.5%.

At this point, the sample consisted of 73.5 mg of protein in the lithium-borate buffer. Vertical zone electrophoresis was carried out on a 3×42 cm column of cellulose. The cellulose powder was equilibrated in the lithium borate buffer, decanted and then packed into the column. The column was washed extensively with the same buffer prior to electrophoresis. The receptor protein was equilibrated in the same buffer by dialysis. The conditions of electrophoresis were 60-80mA, 300-315 volts, 72 hours duration. The column was eluted with the lithium borate buffer. Fractions containing the receptor were concentrated by ultrafiltration and chromatographed on Ultrogel AcA34 columns in the lithium borate buffer to remove excess Triton and to concentrate into a smaller volume. At this stage, the purified produce weighted 6.52 mg. The binding capacity of the original 7,000×g supernatant, the first Ultrogel fraction and the product at this stage were approximately 5.15, 310 and 2,681 pMhCG/mg protein (affinity constant (Kd) of $0.76 \times 10^{-10}$ liter $M^{-1}$), respectively, which represents approximately an 11,805-fold purification of the protein in the 7,000×g supernatant and a final 536-fold increase in receptor binding capacity.

A further purification step was carried out by immuno-affinity column chromatography on hCG bound anti-hCG Sepharose-4B matrix. The receptor specific activity as compared to the zone electrophoresis product increased only by 1.05 fold.

The molecular weight of the aggregate of the electrophoretically pure receptor glycoprotein was found to be about 5.9 million using gel permeation chromatography, as described more fully hereinafter. Purification has advanced to the degree that analysis of the receptor material by disc-gel electrophoresis following treatment hereinafter disclosed yielded a single glycoprotein-band, of about 280 thousand molecular weight. (All molecular weights, amino acid analyses and carbohydrate analyses of the receptor protein and components thereof disclosed herein are understood to be within the normally accepted error of 10% of the value disclosed.) Various protein markers were used to estimate the aggregate molecular weight as well as the molecular weights of the various aggregate oligomers and subunits disclosed hereinafter. Accordingly, one embodiment of this invention involves the use of an electrophoretically homogeneous hLH-hCG receptor glycoprotein of about 5.9 million molecular weight composed of a plurality of glyco polypeptide components, probably linked to one another through di-sulfide bonds to form said glycoprotein aggregate, said glycoprotein aggregate component appearing as a single entity as determined by disc-gel electrophoresis.

Although it is believed that the isolated receptor could be obtained from the corpus luteum of various species of animals having the common receptor for hLH and hCG, as well as from other receptor sources such as those disclosed hereinbefore (and also could be synthetically produced following further structural analyses such as amino acid sequence) the present inventors obtain it from bovine *Corpora lutea*. Thus, a more specific embodiment of the receptor for use herein involves a detergent solubilizable, electrophoretically pure, hCG-hLH receptor glycoprotein of bovine corpora lutea, as above defined, and having a specific binding capacity of at least 2000 pM hCG/mg protein, preferably at least 2500 pM hCG/mg protein.

Binding capacity was performed in albumin by equilibration of the protein sample with approximately 50,000 cpm equivalent to 1.25 ng of $^{125}$I-hCG, in the presence of increasing concentrations of unlabeled hCG from 0.25 to 20,000 ng. Conventional incubation procedures were used, with the addition of an equal volume of 15% (w/v) polyethylene glycol 6,000, dissolved in phosphate buffered saline, to the incubate to precipitate the hormone-receptor complex. Thereafter, the tubes were shaken, centrifuged and the supernatant aspirated. Sediments were resuspended in buffer, again mixed with the polyethylene glycol and recentrifuged. Radioactivity of the pellet, representing $^{125}$I-hCG receptor complex was determined. Specific binding and affinity constants were calculated according to the method of Scatchard, G., *Ann., N.Y. Acad. Sci.*, 51:660 (1949).

Disc-gel electrophoresis was carried out using sodium dodecyl sulfate (hereinafter "SDS")-polyacylamide gel disc electrophoresis as follows:

The purified hLH-hCG receptor fraction was analyzed by SDS-polyacrylamide disc-gel electrophoresis, according to the method of King and Laemmli, *J. Mol. Biol.*, 62:465 (1971) with minor modifications, to yield an optimum resolution of protein components. Aliquots of 30–60 μg of purified fractions of the hLH-hCG receptor were solubilized in 0.5% Triton X-100, lyophilized and dissolved in 100 μl of water. Samples were then dialyzed for 48 hours against 0.125 M Tris-HCl buffer (pH 8.0, containing 1 mM EDTA). Samples were heated in boiling water in the presence of 2% SDS alone or 2% SDS and 1% mercaptoethanol (M.E.), for 1 ½ minutes. Protein markers of known molecular weights dissolved in Tris-HCl buffer and treated with 2% SDS and 1% M.E. were applied on the stacking gel and electrophoresed simultaneously. The electrophoreses were performed in 0.025 M Tris-glycine buffer (pH 8.3, containing 0.1% SDS). After the electrophoreses, the gels were removed from the glass columns and the protein bands were stained with Coomassie-Blue. The relative mobilities ($R_f$) of the protein markers and of the purified receptor fractions were calculated, and a relationship was established between the $R_f$ and logarithm of molecular weight of each marker protein, to calculate the molecular weights, of the purified receptor samples. The 5.9 million aggregate sample treated with 2% SDS yielded a single glycoprotein band of approximately 280,000 molecular weight. The sample treated with SDS plus M.E. yielded three bands of approximately 160,000; 57,000 and 44,000 molecular weights, suggesting the presence of oligomers, probably disulfide linked.

Prior to disc-gel electrophoresis, the receptor protein obtained after cellulose zone electrophoresis was subjected to gel permeation chromatography on a column of Sepharose-4B to determine molecular weight. After gel filtration, the unretarded fraction of receptor protein is the 5.9 million molecular aggregate, as above disclosed. The column was eluted with 10 mM Tris-HCl buffer (pH 7.2, containing I mM MgCl$_2$, 0.0170 NaN$_3$ and 0.5% Triton X-100).

Further experimentation was carried out to determine the components or units forming the 5.9 million aggregate. In each case, the molecular weight estimate was determined using gel permeation chromatography as described below.

Attempts were made to deaggregate the 5.9 million molecular weight protein into its largest polypeptide units.

Gel permeation chromatography of the receptor glycoprotein was carried out before and after the various treatments described below. (A protein concentration of approximately 1 mg/ml was used for each treatment.) In each case, the gel columns were equilibrated and eluted with appropriate solvents containing 0.5% Triton X-100. Standards of known molecular weight (DNA (supercoiled) blue dextran, thyroglobulin, ferritin, aldolase and catalase) were gel-filtered through the columns and gels selected to resolve the approximate range of the molecular sizes of a protein marker. The $K_{av}$ (index of solute migration in gel chromatography) for each marker and for each receptor component was calculated from its elution volume. The molecular weights of the receptor components were determined from a standard curve of $K_{av}$ versus the molecular weights of the known protein markers.

Treatment with 1M NaCl overnight at 4° as well as with 2% SDS and 1% mercaptoethanol at 4° did not alter the molecular weight of the receptor protein aggregate. However, treatment with 2% SDS, at 100° for 1 ½ min. deaggregated the 5.9 million molecular weight material into a plurality of a 280,000 molecular weight species, which was separated on a Sepharose-6B column, of the hormone-free hLH-hCG receptor. The Sepharose-6B column was eluted with 0.1M acetic acid containing 1 mM MgCl$_2$, 0.01% NaN$_3$, 0.1% SDS and 0.5% Triton X-100. When the 280,000 molecular weight species was incubated with $^{125}$I-hCG, and, applied to a Sepharose-6B column, a major hormone-bound component with a molecular weight of 185,000 was recovered by elution with 10 mM Tris-HCl buffer (pH 7.2, containing 1 mM MgCl$_2$, 0.01% NaN$_3$ and 0.5% Triton X-100). If a molecular weight of 40,000 is subtracted for hCG from the 185,000 molecular weight species, the resulting molecular weight of 145,000 suggests the presence of a dimer of the receptor of approximately 280,000 molecular weight. That is, the 280,000 species dissociates into two oligomers of approximately 145,000 molecular weight each. Both the binding of $^{125}$I-hCG or covalent linking of $^{125}$I-hCG alone cause the reduction of the 280,000 molecular weight dimer, and the appearance of the hormone-bound 185,000 molecular weight forms of the receptor.

In another set of experiments, the 280,000 molecular weight component following treatment for 1 ½ min at 100° with 2% SDS and 1.5 mM DTT (dithiothreitol) followed by gel filtration on a column of Ultrogel AcA-34, yielded a 120,000 molecular weight species of the hLH-hCG receptor by elution with a 0.01 M Tris-HCl buffer (pH 7.2, containing 1 mM MgCl$_2$, 0.01% NaN$_3$, 0.01% SDS, 2 mM DTT and 0.5% Triton X-100). Further treatment of the 120,000 species with 50 mM DTT for 1 ½ min at 100°, and gel filtration on Ultrogel AcA-34 in the above 0.01M Tris-MCl buffer yielded two oligomers of the molecular weights 85,000 and 38,000. Each of these components bound $^{125}$I-hCG specifically and eluted from Ultrogel AcA-34 by 10 mM Tris-HCl buffer (pH 7.2, containing 1 mM MgCl$_2$, 0.01% NaN$_3$ and 0.5% Triton X-100) as hormone-bound complexes of molecular weights of 125,000 and 92,000, respectively.

In another experiment, $^{125}$I-hCG was coupled covalently to the 5.9 million molecular weight aggregate, which was then dissociated into hormone-bound 185,000 molecular weight species, but treatment with 2% SDS, for 1 ½ min. at 100°. A 3,000 rpm supernatant thereof was applied to a column of Sepharose-6B and in addition the sediment was redissolved in 10 mM Tris-HCl buffer (pH 7.2, containing 0.5% Triton X-100) and then treated with 2% SDS for 1 ½ minutes at 100° C. followed by gel filtration on the same type column. In both instances, the 185,000 molecular weight species was obtained by elution with 10 mM Tris-HCl buffer (pH 7.2, containing 1 mM MgCl$_2$, 0.01% NaN$_3$, 0.1% SDS and 0.5% Triton X-100).

Treatment of the $^{125}$I-hCG coupled species with 50 mM DTT for 1 ½ min at 100° also yielded $^{125}$I-hCG-coupled oligomers of the molecular weights of 110,000 and 74,000 (corresponding to 70,000 and 34,000 molecular weight units after subtracting 40,000 for hCG). Treatment of the 85,000 and 38,000 molecular weight units with up to 150 mM DTT in the presence of 2% SDS for 1 ½ min at 100°, did not dissociate these units further into smaller molecular weight components. Hence, it is expected that the 70,000 to 85,000 and the 34,000 to 38,000 molecular weight species are probably the disulfide linked subunits of the 120,000 to 140,000 molecular weight component and may be the smallest intact polypeptide units which carry out the specific binding with hCG and hLH.

From the above experiments and discussion, the two lowest molecular weight units known at this time of the naturally-occurring receptor may be defined with respect to their freedom from hormone units, their molecular weight ranges of about 34,000 to 38,000 and about 70,000 to 85,000, respectively, their specific binding capability for hCG and their stability under the various conditions of treatment heretofore described. In turn, these basic units appear to be linked through covalent disulfide bonds into repeating units of about 120,000 to 140,000 molecular weight. At the present time, it is believed that one each of the two types of basic units join to form the 120,000 to 140,000 molecular weight unit. Variations in molecular weight determinations are believed due to the limitations of the disc gel electrophoresis and gel chromatography systems, including the number of different standard protein markers employed. However, the important determinations are that two different molecular weight subunits, each having specific hCG binding capability exist which in turn form the basic repeating building blocks of the receptor. The 120,000 to 140,000 molecular weight species is in a sense a repeating monomeric unit, two of which link to form a 240,000 to 280,000 molecular weight oligomer. A plurality of these oligomers are associated with one another to form the 5.9 million aggregates.

Amino acid and carbohydrate analyses were carried out on the electrophoretically pure receptor product and on some of the partially purified intermediate receptor products. Amino acid analysis was carried out by dialyzing 100 μg aliquots of receptor overnight against water, drying in vacuo and hydrolyzing with 100 Ml of 5.7N HCl at 110° for 24 hr. The hydrolysate was dried again in vacuo to remove any residual acid. The sample was dissolved in citrate buffer, and analyzed for amino acids on an automatic amino acid analyzer (Durrum, Model D-500).

The neutral sugar content of the hLH-hCG receptor was determined by methanolysis of the sugars, trimethysilylation and gas liquid chromatography. The hexosamine content was determined on the amino acid analyzer after a 4 hour hydrolysis of the sample with 5.7N HCl. The sialic acid content of the purified receptor was determined by the thiobarbituric acid method.

The major amino acids found in the electrophoretically pure receptor are aspartic acid and glutamic acid. On a percentage basis, there is somewhat less of each in comparison with a sample purified by the sequential method of the Reference Example but substituting affinity chromatography for zone electrophoresis. The carbohydrate content of the electrophoretically pure receptor is approximately 10%. See Table 1 setting forth amino acid and carbohydrate analysis of three receptor materials. The number of each type of amino acid residue in the glycoprotein aggregate can be calculated from Table 1.

The electrophoretically pure glycoprotein receptor aggregate acts as an antigen when administered to test animals, such as rabbits, for production of antiserum. The various glycoprotein subunits of the aggregate, as disclosed hereinbefore, also elicit antigenic response in test animals.

TABLE 1

AMINO ACID AND CARBOHYDRATE ANALYSES OF THE hLH-hCG RECEPTOR

| | Ultrogel AcA-34* | Affinity Chromatography** 9/100 g Protein | Zone-electrophoresis (without final immuno-affinity chromatography step) |
|---|---|---|---|
| Amino Acid | | | |
| ASPARTIC | 8.7 | 9.4 | 9.1 |
| THREONINE | 4.0 | 5.6 | 5.3 |
| SERINE | 3.9 | 4.6 | 5.8 |
| GLUTAMIC | 13.6 | 12.6 | 12.1 |
| PROLINE | 9.0 | 8.7 | 5.2 |
| GLYCINE | 3.8 | 4.7 | 4.5 |
| ALANINE | 4.6 | 5.4 | 4.8 |
| VALINE | 6.0 | 5.1 | 8.3 |
| CYSTEINE | Not detectable | Not detectable | |
| Cysteic Acid | trace | 1.3 | 2.4$^a$ |
| METHIONINE | 1.5 | 1.7 | 2.3 |
| ISOLEUCINE | 4.9 | 5.5 | 4.4 |
| LEUCINE | 11.7 | 9.6 | 8.7 |
| TYROSINE | 3.4 | 4.3 | 4.9 |
| PHENYL-ALANINE | 5.1 | 6.0 | 5.0 |
| LYSINE | 7.3 | 6.9 | 7.0 |
| HISTIDINE | 3.6 | e | 2.8 |
| ARGININE | 7.5 | 7.6 | 7.4 |
| Carbohydrate | | | |
| Fucose | Not detectable | Not detectable | |
| Mannose | 1.2 | 1.1 | |
| Galactose | 0.7 | 1.6 | |
| N-acetyl-glucosamine | 1.1 | 3.7 | |
| N-acetyl-galactosamine | 0.3 | 2.6 | |
| Sialic acid | 0.5 | 1.9 | |

$^a$Determined on a separate aliquot after performic acid oxidation
e Eluted with detergent
*Intermediate sample of Reference Example type sequence up to and including the chromatographic step using Ultrogel AcA-34 but prior to further purification
**Reference Example type sequence carried out up to the chromatographic step using Ultrogel AcA-34 and followed by affinity chromatography instead of zone electrophoresis The most preferred receptor purification method involves the steps of:
(1) homogenizing a receptor source material in an aqueous medium to disperse the receptor in a liquid aqueous fraction;
(2) separating membrane-bound protein containing the receptor from the liquid aqueous fraction:

(3) dispersing the membrane-bound protein in an aqueous medium and extracting the aqueous medium with an organic solvent in which lipids are soluble to remove lipid from the aqueous phase:
(4) separating the aqueous phase containing the receptor from the remainder of the product of step (3) and concentrating the aqueous phase: and
(5) fractionating the aqueous phase based upon molecular weight to remove inert proteins and concentrating the receptor fraction.

It is preferably in the present invention that the process further comprises the steps of:
(6) subjecting the receptor fraction to electrophoresis to separate said fraction from other remaining protein fractions; and
(7) purifying the receptor fraction by subjecting it to immuno affinity chromatography.

REFERENCE EXAMPLE 2: RECEPTOR PURIFICATION

FIG. 1 is a flow diagram of the most preferred receptor purification method of the present invention which is described in detail below.

A batch of 1200 g of fresh bovine ovaries stored at $-60°$ C. were thawed. *Corpora lutea* (200 g) were dissected and homogenized with 1500 ml of 10 mM Tris-HCl buffer (pH 7.2, containing 20% glycerol, 1 mM $MgCl_2$, 0.1% $NaN_3$ and $10^{-6}M$ leupeptin). The homogenate was centrifuged at 164 $\times g$ for 30 min to remove cell debris, and to recover more than 90% of protein hormone binding activity. The supernatant was further centrifuged at 16,300 $\times g$ at 4° C. for 2 ½ hr. Almost 30% of proteins with 80% of hormone-binding activity were sedimented, and 70% of proteins with 20% of hormone-binding activity was removed in the supernatant which was discarded. The LH-hCG receptor in the sediment was solubilized in 1,000 ml of 10 mM Tris-HCl buffer (pH 7.2, containing 1% Triton X-100. 1 mM $MgCl_2$, 0.01% $NaN_3$ and $10^{-6}M$ leupeptin) by sonicating three times for 10 seconds each time at pulses of 50 watts followed by stirring in ice for 1 hour. Up to 50–60% of proteins were solubilized with 80% recovery of the LH-hCG binding activity. In order to remove the free lipids from the crude receptor solution. 500 ml of chilled redistilled petroleum then was mixed with the solubilized receptor. After stirring for 30 min. at 4° C. the petroleum ether treated receptors was centrifuged at 16,300$\times g$ for 1 hour at 4° C. The soluble LH-receptor was recovered in the aqueous layer.

The aqueous layer containing soluble LH-hCG receptor was then concentrated through a PM-30 membrane to reduce the volume to about 300 ml, then applied to a 9$\times$90 cm column of Sepharose-6B equilibrated with 10 mM Tris-HCl buffer (pH 7.2, containing 0.5% Triton X-100, 1 mM $MgCl_2$, 0.01% $NaN_3$ and $10^{-6}M$ leupeptin) at 4° C. The column was eluted with the same buffer. The soluble LH-hCG receptor was separated into three major protein fractions by gel filtration on Sepharose-6B. The fractions were analyzed for protein concentration and tested LH-CG binding activity. Unretarded fraction I contained most of the LH-hCG receptor with protein recovery of about 14%. Fraction II and III contained the majority of proteins without hormone-binding activity. Therefore, gel filtration on a column of Sepharose-6B was an effective step to remove inert proteins.

Fraction I from the Sepharose-6B column was concentrated five fold by ultrafiltration through a PM-30 Amicon filter to a protein concentration of 1.0 mg/ml, and mixed with equal volume of 30% polyethylene glycol 6,000 (PEG) and stirred for 20 min. at 4° C. The precipitate was recovered by centrifugation at 16,000$\times g$ for 1 hour at 4° C. The precipitate was redissolved in Tris-HCl buffer (pH 7.2, containing 0.5% Triton X-100 and 1.0 M NaCl) by stirring for 1 hour at 4° C. and for 20 min. at room temperature. The solubilized fraction was applied to a 5$\times$50 cm column of Ultrogel AcA-22 (Pharmacia) equilibrated with Tris-HCl buffer. The column was eluted with the same buffer at a flow rate of 10 ml/20 min. in a refrigerated fraction collector. The fractions were pooled and analyzed for protein content and hCG binding activity. The active fraction I from the Ultrogel AcA-22 column was precipitated at a final concentration of 15% PEG. The precipitate was dissolved in Tris-HCl buffer (pH 8.3, containing 0.5% Triton X-100) to yield a protein concentration of 3–6 mg/ml.

Then, zone electrophoresis was performed to discriminate proteins based on charge. More specifically, a 4$\times$35 cm cellulose column was equilibrated with 10 mM Tris-HCl buffer (pH 8.3, containing 1 mM $MgCl_2$, 0.01% $NaN_3$ and 0.5% Triton X-100). An aliquot of up to 200 mg protein of the LH-hCG receptor fraction I from Sepharose-6B was applied onto the cellulose column in a volume of 20–30 ml. Electrophoresis was performed at a constant voltage of 30 v for 76 hours at 4° C. At the end of the electrophoresis, the column was eluted with the same buffer at a flow rate of 5 ml per 20 min. Each protein fraction was pooled on the basis of absorbency of 280 nm and the $^{125}I$-hCG-binding activity. Only fraction II contained the receptor with hormone-binding activity which was concentrated by ultrafiltration through a PM-30 Amicon filter and stored in a lyophilized state at 4° C. until use.

AcA-22 chromatography was repeated as described above to remove impurities (buffer salts and excess Triton X-100) resulting from the zone electrophoresis.

Next, affinity chromatography was performed to verify the purity of the receptor. More specifically, highly purified hCG was covalently linked to CNBr-activated Sepharose-4B by the procedure recommended by the supplier (Pharmacia). Fraction II from the zone electrophoresis column, containing the LH-hCG receptor, was applied to the affinity column and the column was eluted at a flow rate of 0.5 ml/min. The column was washed with the buffer until no proteins were eluted. The LH-hCG receptor was eluted with 10 mM Tris-HCl buffer (pH 4.0 (adjusted with acetic acid). containing 0.5% Triton X-100, 0.5 M NaCl). The column was eluted at a flow rate of 4 ml/10 min. Each fraction was immediately adjusted to pH 7.2 with 1M NaOH. Fractions containing LH-hCG receptor were pooled and concentrated.

Analysis of the purified LH-hCG receptor from the affinity chromatography on SDS-polyacrylamide gel electrophoresis as described above revealed a single band attesting to the purity of the LH-receptor.

The second antigen component used herein is hCG. Although it may be possible to use naturally occurring hCG, preferably the $\beta$ subunit, or a derivative or fragment thereof, in modified or unmodified form, is employed to reduce generation of antibody cross-reactive with hLH and/or other hormones which include the non-specific $\alpha$-subunit. The hCG antigen can be obtained commercially purified and the hCG-$\beta$ prepared as known in the art. For example, see the description of Bahl U.S. Pat. No. 4,310,455, beginning at column 4, line 23, and the procedures of Swaminathan and Bahl, *Biochem. Biophys. Res. Comm.*, 40:422, 1970 and Bahl, *Hormonal Proteins and Peptides*, C.H. Li. ed., Acad. Press. page 170, 1973, referenced in said Bahl patent.

Although the invention has been disclosed with respect to the preferred use of the electrophoretically homogeneous receptor and/or subunits thereof, it should be understood that various receptor derivatives and fragments could be employed in the practice of the present invention as long as the particular derivative or fragment utilized still possesses the ability to elicit an antigenic response in the production of antibody to the hCG receptor site. Various chemical and enzymatic modifications and digestions can be employed to prepare receptor derivatives and fragments. In a similar manner. the preferred hCG-$\beta$ employed as a reagent herein can be utilized as such, or in the form of a derivative or fragment thereof, particularly those disclosed in the prior art as having increased immunospecificity and/or increased antigenic properties. Chemical modification, enzymatic cleavage and the like can be carried out prior to conjugation with the purified hLH-hCG receptor. For example, the various alkylated hCG-$\beta$ derivatives of Bahl, the further purified hCG-$\beta$ of Talwar and the like can be employed in the present invention. The receptor or its oligomeric components or after their modification may have preferential sites, specific only for hCG alone.

Many different procedures are known for linking or complexing a hormone-type unit with a protein. Basically, any of the procedures known in the prior art for conjugating one protein with another can be employed herein. Covalent bonding, ionic bonding, Van de Waals forces and the like, alone or in combination, can be employed to form the hCG $\beta$-receptor antigen conjugate or complex. What is needed is to insure that where the dual function antigen is desired, that the coupling mechanism utilized is sufficient so that substantially all of the antigen material can circulate intact. This is particularly important where a passive immunization technique is to be employed. That is, through the use of the dual function conjugated antigen, a dual function antibody can be secured and then utilized as a contraceptive vaccine.

Thus, conjugation or linking of hCG, preferably hCG-$\beta$ or a derivative or fragment thereof, with the receptor can be carried out utilizing any standard procedure, such as by reacting hCG-$\beta$ and the receptor in aqueous medium with one of the bi-functional cross linking reagents disuccinimidyl suberate (hereinafter "DSS"), dithiobis (succinimidyl propionate) and N-succinimidyl 3-(2-puridylthio) propionate. See Carlsson et al. "Protein-Thiolation and Reversible Protein-Protein Conjugation", *Biochem. J.*, 173:723 (1978), and Rebois et al, "Covalent Cross Linking of Human Chorionic Gonadotropin to Its Receptor in Rat Testes", *Proc. Nat. Acad. Sci. U.S.A.*, Volume 78, No. 4, p. 2086 (Apr. 1981). Other techniques that could be used would be to carry out the reaction utilizing as the linking agent glutaraldehyde according to Avarameas, S. *Immunochem.*, 6:43 (1969) or with a water soluble carbodiimide according to Cuatracasas P. and Anfinsen, C.B., *Methods of Enzymology*, XXII:343 (1971). Other procedures using reagents such as ethylchloroformate, bifunctional arylhalides, such as 1,3 or 1,4 di fluoro- or dichloro-benzene, 2,4 difluoro- or dichlorotoluene, 4,4[1] difluoro- or dichloro-bi-phenyl and the like, 1,5-difluoro-2,4-dinitrobenzene, bifunctional isocyanates, such as toluene 2,4-diisocyanate, toluene 2,6-diisocyanate, 4,4[1]-diisocyanatodiphenylmethane, hexane 1,6-disocyanate and the like, and bifunctional acylating agents such as di-acid halide, carboxylic dianhydrides, dicarboxylic acids, and esters and diamides, and imiidoesters, etc. may also be used.

At the present time, the preferred conjugation procedure utilizes DSS.

REFERENCE EXAMPLE 3: FORMATION OF hCG-RECEPTOR UNIT

In this experiment, hCG-$\beta$ and the electrophoretically homogeneous 5.9 million molecular weight receptor aggregate were utilized. hCG-$\beta$ and the receptor were separately suspended in phosphate buffered saline at a concentration of approximately 1 milligram of protein per milliliter. DSS was dissolved in dimethyl sulfoxide at a concentration of 50 mM (1.8 mg DSS/100 ml), the solution of DSS being added to a protein suspension containing 1.5 mg of hCG-$\beta$ and 1.0 mg of the receptor so that the concentration of dimethylsulfoxide in the final solution is 2%. The mixture was incubated at 25° C. for 15 minutes. Any non-conjugated hCG was dissociated by dilution of the sample with an equal volume of 4M $MgCl_2$. Then, a second incubation was carried out at 4° C. for 10 minutes, followed by centrifugation at 5,000$\times$g for 15 minutes.

The solution was subjected to Sepharose-6B chromatography using a column of 1$\times$60 cm. The Sepharose-6B column was eluted with 0.01M Tris HCl buffer (pH 7.2, containing 1 mM $MgCl_2$, 0.01% $NaN_3$ and 0.5% Triton X-100). Collection was at a flow rate of 1.5 ml/tube/15 minutes. Various fractions were analyzed for hCG-$\beta$ presence and receptor presence by utilizing standard radioimmunoassay techniques for hCG-$\beta$ and standard radioreceptor assay techniques for the receptor. In this experiment, a fraction comprising tubes 22 and 23 contained significant hCG-$\beta$ and receptor antigenic activities. Remaining collected fractions possessed binding activity for hCG-$\beta$ but did not possess binding activity for the receptor, indicating the separation of excess hCG-$\beta$ from the conjugate.

As discussed above, the hCG and receptor antigens, separately or in conjugated form, may be used to produce antibodies to both hCG and the receptor either in lower animals, whereby an antiserum useful as a vaccine in humans or animals is produced or the antigen materials may be administered directly to humans or animals, in which case the antibodies would be produced in humans or animals. In either case, the antiserum is being utilized for prevention or termination of pregnancy.

The antiserum can be prepared by conventional procedures utilized in the preparation of other types of antibody serum in lower animals. That is, a host animal such as a horse goat, sheep, rabbit, monkey, pig or the like is injected with antigen on a regular basis until the blood thereof contains the desired level of antiserum. The injection schedule for the antigen is not critical, it may be injected as often as practical. In practice, injection every other week usually proves to be satisfactory. Longer or shorter periods between injections are, of course, possible. The dosage of antigen is, of course, proportionate to the weight of the host animal. The minimum dosage is that required to induce an antibody response in the host, while the maximum is that at which no adverse side reactions occur. In practice, dosages from about 2 μg/kg to about 50 μg/kg of body weight will usually prove satisfactory. The injections are continued until the desired antisera level in the blood serum is attained. Generally, an antisera titer of from 1:5,000 to 1:10,000 would be considered satisfactory.

When the desired titer is achieved, a quantity of blood is withdrawn from the host animal. The serum portion of the blood is then recovered. The quantity of blood removed is a function of the total volume of blood in the host animal. Generally, up to about 12 volume percent of the blood may be removed at any time without the host animal suffering excessive adverse effects. Thus, if the host animal is a rabbit, from about 20–40 ml blood will be removed.

The serum can be recovered by simply allowing the blood to coagulate and then decanting the blood serum. Various conventional purification steps can be utilized.

A typical immunization procedure using rabbits is as follows: 100 micrograms of the antigen material in 0.5 ml saline is mixed with an equal volume of Freunds complete adjuvant to form an emulsion. The emulsion is injected at 10-20 sites intradermally and subcutaneously. The injection schedule is repeated every other week using one-half the original amount of the antigen materials at two sites subcutaneously or intramuscularly. The serum samples are collected every other week from an ear vein and are tested for binding using radioactive assays for both hCG and the receptor. One regimen for raising the antibody is that disclosed in Avarameas et al, *Immunochem.*, 6:53 (1969).

In using the vaccines of the present invention to prevent or terminate pregnancy, either the antibodies themselves are administered to a female or the antigen(s) are administered to a female to provoke the formation of antibodies therein. In either case, antibodies are present in the female to effectively neutralize hCG and also to prevent hCG from interacting with the hCG-hLH receptors of the corpus luteum and of the placenta. The prior art, such as the Bahl and Talwar patents discussed hereinbefore, disclose appropriate techniques and levels of hCG-β antigen to be utilized in contraceptive vaccine regimens. Similar levels of administration are contemplated herein.

The hCG-receptor unit or the receptor alone can be employed when administered in a pharmaceutically effective amount as a contraceptive vaccine. Generally, a pharmaceutically effective amount will vary depending upon the age, weight and species to which the hCG-receptor unit or receptor is administered. Generally, a dosage in the range of 100 μg to 200 μg is employed, preferably 50 μg to 100 μg.

In preferred embodiments of this invention, the antibody levels maintained in the female would be less than that required with the hCG-β vaccines of the prior art because of the dual function of some of the antibodies in the present invention, that is not only to neutralize hCG but also to block receptor sites. The dual action will compensate for the low titer of the antibody and will permit negligible cross reaction with hLH. The hLH excess during the preovulatory phase should overcome the immunological block, and it is expected that ovulation will not be impaired.

As discussed above, the present invention is not limited to a contraceptive vaccine for humans, i.e., it is also applicable for veterinary use as a contraceptive vaccine in dogs, cats, cows, sheep, pigs, etc.

In the vaccine embodiments of the present invention, the antigens and/or antibodies used are administered in a pharmaceutically acceptable carrier, such as the various aqueous and lipid media, such as sterile saline, utilized for preparing injectables to be administered intramuscularly and subcutaneously. Conventional suspending and dispersing agents can be employed. Other means of administration such as implants, for example a sustained low dose releasing bio-observable pellet, will be apparent to the skilled artisan.

It is preferable in the present invention to employ silastic implants containing the receptor unit or receptor of the present invention. These implants can be used subdermally with lyophilized powder of the receptor unit or receptor. Body fluid such as plasma can pass through the silastic implant and pick up, as a carrier, small amounts of the receptor unit or receptor.

REFERENCE EXAMPLE 4: FORMATION OF SILASTIC IMPLANTS

The silastic implants of the present invention can be prepared by, for example, solubilizing highly purified receptor in 10 mM Tris-HCl buffer (pH 7.5, containing 0.5% Triton X-100) in an appropriate concentration. Silastic tubing cut into 0.3 cm × 10 cm pieces can be slit horizontally on one side to allow the tubing to be pried open like a sheet. The sheet can roll back into the form of tube again. An elastic needle heated at 90° C. can be used to pierce 10–20 pin holes in the tubing to allow the material to flow out easily from the implant under the skin. The inner volume (mm$^2$) of the silastic tube can be calculated from the formula $\pi \times r^2 \times h$. The concentration of the receptor solution can be adjusted such that the volume (mm$^2$) of the silastic tubing contains about 2.5 mg of receptor. The receptor solution can be sterilized by ultrafiltration through a 0.45 Amicon filter prior to use. Silastic tubes of 0.3 mm × 10 mm can be placed in a vial in an upright position tightly against each other so as not to tilt. The receptor solution can then be poured into the vial to cover the silastic tubing. Any air bubbles trapped in the tubing can be removed by suction with the aid of a syringe to allow the silastic tubing to be completely filled with the receptor solution. The solution can then be frozen and lyophilized under sterile conditions. The resulting silastic implant will contain about 2.5 mg of the lyophilized receptor. The implants can be stored individually in free load trocars for implantation at 4° C. in a dessicator under sterile conditions. The silastic implants of the present invention can last from 6–12 months in a human or animal and can be replenished with fresh lyophilized powder of the receptor unit or receptor if necessary.

With decaying titers of antibody employed in the present invention or with the implants employed in situ in the present invention, the hormonal profiles and the return of cyclicity in the menstruation and perineal swelling can lead to the reversibility of infertility brought about by the contraceptive of the present invention.

Although the present invention has been disclosed with particular reference to contraceptive use in human and animal breeding the antigens used herein, particularly the conjugate would also have utility in other areas related to the treatment of gonadotropic hormone dependent cancers and the like, the diagnostics and management of reproduction, namely gonadal function, ovulation, abnormal pregnancy, disorders of hormonal production and spermatogenesis in the male.

The following examples are provided to illustrate the use of the present invention as a contraceptive vaccine and are in no way intended to limit the scope of the present invention.

EXAMPLE 1

Active Immunization in Rabbits

Highly purified LH-hCG receptor was prepared as described in Reference Example 2. Three New Zealand white adult female rabbits of approximately 3 kg of body weight, designated as A, B and C, were boarded in an animal facility for active immunization against the receptor by multiple site subdermal injections to produce antibodies and observe the effect of endogenously produced antibodies on the reproductive functions of the rabbits. An aliquot of 100 μg protein equivalent of receptor suspended in 100 μl of 0.9% (w/v) saline was emulsified with 100 μl of complete Freund's Adjuvant and used for initial immunization by intradermal injections of 10-20 μl of the immunogen at multiple sites. Afterwards, aliquots of 100 μg of receptor emulsified in adjuvant as above were injected subcutaneously at four week intervals for a period of five and a half months. Rabbits were bled by the ear vein puncture at four week intervals after the first immunization. The blood was centrifuged at 3,400 rpm for 15 minutes at 4° C. The serum was separated and stored at −20° C. until analyzed.

The gamma-globulin fraction was isolated from the sera of immunized rabbits by Rivanol precipitation according to the method of Horejsi, J. S. et al *Acta Medica Scan.*, 155:65–70 (1956). After removal of the Rivanol the gamma-globulin fraction was concentrated in an Amicon ultrafilter using a PM-10 membrane. The gamma-globulin fraction was gel-filtered through a 3×30 cm column of Sephadex G-25 (fine) which was previously equilibrated in 0.1 M ammonium bicarbonate buffer of pH 8.5. The column was eluted with the same buffer. The gamma-globulin eluted in the unretarded protein fraction was lyophilized and stored at 4° C. The protein concentration in the gamma-globulin fraction was determined by the method of Lowry, C. H. et al, *J. Biol. Chem.*, 193:265–275 (1951).

The antisera samples and the gamma-globulin fractions were examined for the presence of antibody by (1) the ability to specifically bind $^{125}$I-receptor, (2) the ability to inhibit specific binding of $^{125}$I-hCG to the receptor, (3) the ability to inhibit the production of testosterone by rat Leydig cells stimulated by hCG (Dafau, M. L. et al. *J. Clin. Endocrinol Metab.*, 39:610–617 (1974)), and (4) microplate enzyme immunoassays (Munro, C. et al *J. Endocrinol*, pages 41–49 (1984)).

Separate aliquots of 1 ml each of the antisera were mixed on a Vortex with 0.5, 2.5, 5 and 10 μg of receptor protein as well as 6.25, 12.5 and 50 ng of hCH and incubated for 3 hours at 37° C. The incubates were centrifuged at 3,400 rpm in a Sorvall refrigerated centrifuge for 20 minutes. The supernatants were separately collected and examined for specific binding with $^{125}$I-receptor as well as with $^{125}$I-hCG as discussed in detail below.

Highly purified LH-hCG receptor was labeled with high specific activity $^{125}$I-Na utilizing the chloramine-T method of Hunter, W. M. et al, *Nature* 194:495–496 (1962) as follows. An aliquot of 5 μg of the receptor was dissolved in 50 βl of 0.1M sodium phosphate buffer (pH 7.4, containing 0.1% Triton X-100) in a glass reaction vial. To the vial, 50 βl of 0.1M of sodium phosphate buffer (pH 7.4), 0.5 mci of $^{125}$I-Na and 20 βl of chloramine-T of a concentration of 1 mg/ml were added sequentially. After 1 minute of gentle agitation, 50 βl of a 2 mg/ml sodium metabisulfate solution was added to stop the reaction. An aliquot of 0.5 ml of 0.1M sodium phosphate buffer (pH 7.4, containing 0.1% Triton X-100) was added and mixed to stabilize the reaction mixture. The mixture was filtered through a 1×30 cm column of Ultrogel AcA-34 equilibrated with 0.1M sodium phosphate buffer (pH 7.4, containing 1.0% bovine serum albumin and 0.1% Triton) to separate the labeled receptor from the damaged protein and free $^{125}$I The column was eluted into 0.5 ml fractions with the above buffer. Fractions were tested for specific binding with gamma-globulin isolated from antiserum against the receptor. Fractions with the maximum specific binding were pooled and further purified by gel-filtration again through another column of Ultrogel AcA-34 as described above. Fractions which showed the maximum specific binding were pooled and utilized.

In a competitive protein binding assay, rabbit anti-receptor antibody was examined for binding to the $^{125}$I-receptor and the displacement of the bound $^{125}$I-receptor by unlabeled receptor. More specifically, approximately 50,000 cpm of $^{125}$I-receptor in 100 βl of RIA buffer containing 0.05M sodium phosphate buffer (pH 7.4, containing 0.1% bovine serum albumin (BSA). 0.01% NaN$_3$ and 0.2% EDTA) alone and in the presence of 1.5 μg receptor in 100 μl of RIA buffer were incubated overnight at 37° C. Specific binding was calculated from the decrease in the counts of the total binding in the presence of unlabeled receptor.

Inhibition of binding of $^{125}$I-hCG to the receptor was performed to examine the ability of anti-receptor antibody to inhibit binding of $^{125}$I-hCG to the plasma membrane receptor prepared from bovine *Corpora lutea* and rat Leydig cells. More specifically, approximately 125 μg lyophilized protein aliquots of the plasma membranes were suspended in 100 μl of distilled water and incubated at 4° C. with approximately 50 000 cpm of the $^{125}$I-hCG in 100 μl of 10 mM Tris-HCl buffer (pH 7.2, containing 0.1% BSA, 1 mM MgCl$_2$, 1 mM CaCl$_2$, 0.01% NaN$_3$) for 60 minutes in the presence of 100 μl of various dilutions of antisera against the receptor or various amounts of immuno gamma-globulin in 100 μl of 0.05M phosphate buffered saline (PBS) (pH 7.4, containing 0.1% BSA, 0.01% NaN$_3$ and 0.2% EDTA). Parallel controls were performed using normal rabbit serum and normal rabbit gamma-globulin.

Inhibition of testosterone production by rat Leydig cells by anti-receptor antibody was carried out using Sprague-Dawley male rats between the age of 56–70 days with a body weight range of 250–350 gm. These rats were used to prepare the Leydig- cells by the method described by Dufau, M. L. et al *J. Clin. Endocrinol Metab.* 39, 610–617 (1974). More specifically. Leydig cells were suspended in medium 199 with 26 mM Hepes buffer Hank's salts. L-glutamine (GIBCO). containing 0.125 mM of 1-methyl 3-isobutylxanthine (MIX Sigma) and 0.1% BSA) and pre-incubated for 30 minutes at 34° C. under an air mixture of 95% O$_2$ and 5% CO$_2$ in a metabolic shaker at 150 cycles/minute. The Leydig cell suspension was centrifuged at 120×g. The supernatant was discarded and sedimented Leydig cells were resuspended in the same media containing 2% calf serum (GIBCO) at a concentration of 10 ml per testis and used as the source of receptor. The assay was performed at 37° C. and samples were incubated for 3 hours. Testosterone was measured by a RIA kit obtained from Diagnostic Products Corporation, Los Angeles, Calif.

Figure 2:
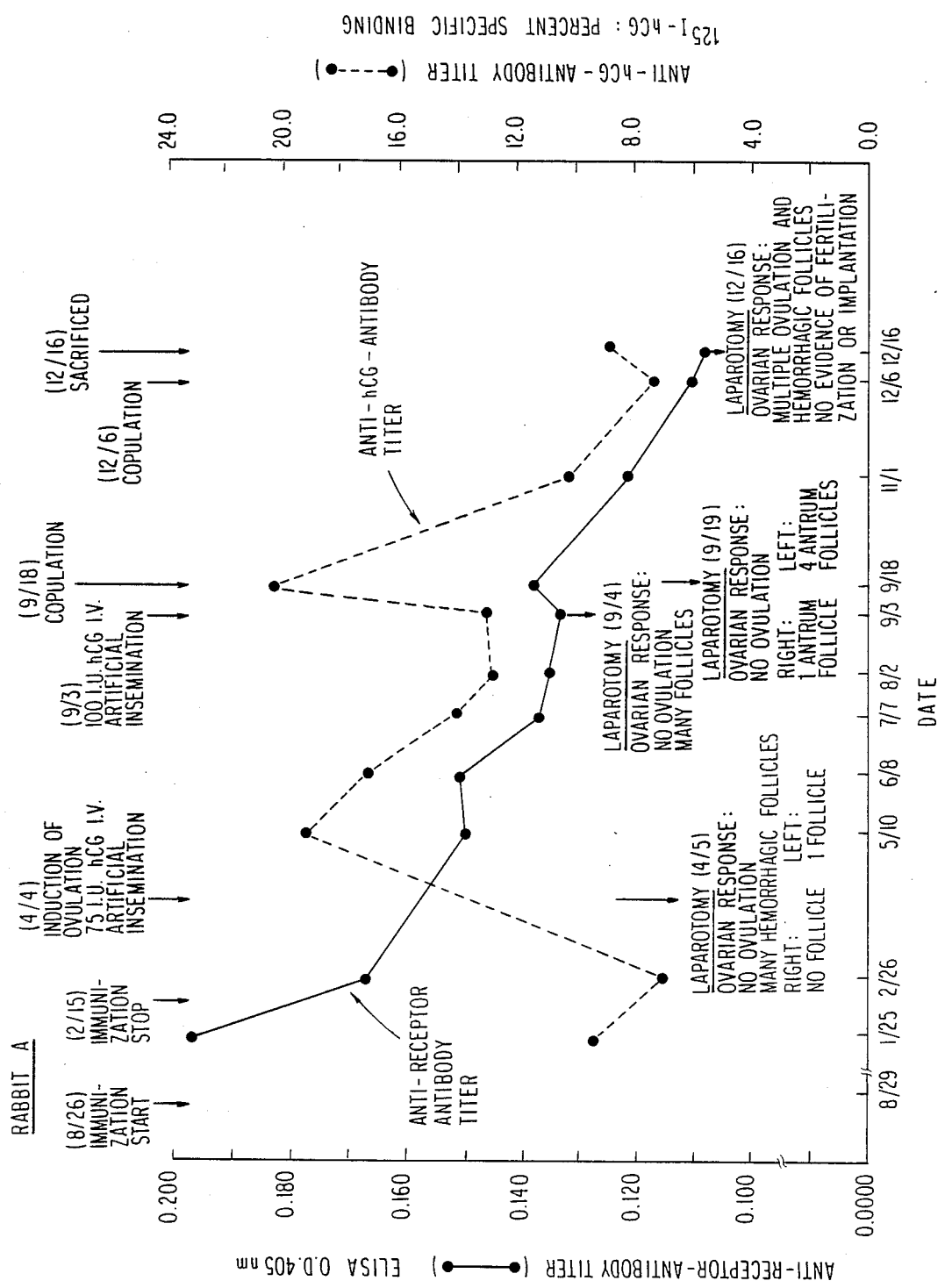
FIGS. 2 and 3 graphically illustrate the effect of endogenous anti-receptor antibody on reproductive functions in female rabbits.

The effects of active immunization against the hCG-LH-hCG receptor complex on the reproductive functions in rabbits namely ovulation, fertilization Corpus luteum formation and implantation were observed in the presence of anti-receptor antibody in the blood circulation of rabbits. The rabbits were induced to ovulate and then artificially inseminated. Laparotomy was performed to observe follicular growth, ovulation Corpus luteum formation as well as implantation of the blastocyst at an appropriate time as described in FIGS. 2 and 3. Specifically, two months after the last immunization, 75 IU of hCG was injected into rabbit A and C via ear vein. The rabbits were immediately artificially inseminated with 2 ml of fresh semen obtained from the epididymis of a fertile male rabbit. The laparotomy was performed 20 hours after the induction of ovulation and artificial insemination. The ovaries were examined for folliculogenesis and ovulation. The status of the uterus was also examined in both the rabbits.

Rabbit C was sacrificed eight days after the laparotomy. Tissue from brain, lung, heart, thyroid spleen, stomach kidney, urinary bladder, ureter, liver, intestine, uteri, cervix and fallopian tube were removed and fixed in 40% formalin for histopathological examination to rule out any toxic effects of antibody against LH-hCG receptor.

Five months after the last immunization, rabbit A was again stimulated with 75 IU of hCG and inseminated as described above. Twenty hours later, a laparotomy was performed and rabbit A was again examined as described above. Two weeks later rabbits A and B were mated with two fertile male rabbits. Twenty-four hours later, rabbits A and B were subjected to laparotomy. Two weeks later another laparotomy was performed and rabbit B was examined for the status of ovaries, corpus luteum formation, evidence of fertilization and implantation. Periodically blood was collected from rabbits A and B and analyzed for antibody titers. The rabbits were subsequently observed to evaluate the reversal of ovarian function and fertility.

The sera samples of rabbits A, B and C obtained prior to immunization and periodically during immunization and after the cessation of immunization were analyzed for $E_2$, P and LH levels by RIA kits. The reagents were supplied by Nuclear Medical Systems Inc., Newport Beach, Calif. LH levels in rabbit sera were estimated by a RIA method. Rabbit LH supplied by NIH (National Hormone and Pituitary Program, Baltimore, Md.) was iodinated by the chloramine-T method described above. Rabbit LH was used for iodination and as a standard.

Rabbits A, B and C showed the presence of receptor antibody in the serum collected during the fourth month subsequent to the first immunization. The antisera from rabbits A, B and C were then examined at four week intervals for specific binding with $^{125}I$-receptor as described above. The results demonstrated that the antibody showed an increasing titer with further immunization. One hundred μg aliquots of the immunoglobulin fractions isolated from the sera of rabbits A and C also showed a specific binding of 18.6 and 15.0 percent, respectively with labeled receptor.

The gamma-globulin fractions prepared with antisera from rabbits A and C were pooled and examined for the ability to inhibit the binding of $^{125}I$-hCG to the receptor in crude plasma membranes, prepared from bovine Corpora lutea and Leydig cells prepared from rat testis as described above. The results demonstrated that there was 31% inhibition of binding of $^{125}I$-hCG to bovine Corpora lutea membranes by 100 μg of gamma-globulin as well as 67% and 85% inhibition in the case of rat Leydig cell membranes by 150 μg and 300 μg of gamma-globulin respectively.

The presence of antibodies against the receptor was further demonstrated when 100 μg of gamma-globulin fraction caused a 41% inhibition in the production of testosterone by rat Leydig cells, stimulated by 50 mIU of hCG as described above.

The anti-receptor antibodies produced in the rabbits also demonstrated cross-reaction with $^{125}I$-hCG, indicating an elaboration of idiotypic antibodies.

Anti-receptor antiserum absorbed with 0.5 μg. 2.5 μg, 5 μg and 10 μg protein equivalent of receptor per ml serum, yielded a progressive decrease in the specific binding of the $^{125}I$-receptor namely, 15.3%, 10.3%, 4.4% and 3%, respectively, as compared to 55.7% specific binding. It may be noted that binding of $^{125}I$-hCG to the unabsorbed and absorbed anti-receptor did not change binding with the unabsorbed anti-receptor antibody. The $^{125}I$-receptor bound to the absorbed anti-receptor anti-serum, was not displaced by the unlabeled hCG. These results further demonstrate that the anti-receptor antibody contained discrete and specific antibodies directed against the LH-hCG receptor. Similarly, after the absorption of the anti-receptor antisera with 6.25, 25 and 50 ng of hCG per ml, the specific binding of $^{125}I$-hCG to absorbed sera decreased to 44.8%, 34.3% and 20.2%, respectively, These observations suggest that the anti-receptor antisera contained a separate entity of antibody which specifically bound hCG.

Induction of ovulation in normal rabbits by the administration of 75 IU of hCG can produce 8 to 10 follicles from each ovary which are fertilized and implanted in the uterus after artificial insemination or mating. Two months subsequent to the cessation of immunization, rabbit A, after induction of ovulation by 75 IU of hCG and artificial insemination, showed no sign of ovulation at the time of laparotomy (see FIG. 2). However, the left ovary of rabbit A contained only one large follicle. These observations clearly showed that the anti-receptor antibody in rabbit A suppressed ovarian function and caused a state of infertility. Uteri in both rabbits were normal in size and appearance and there was no evidence of fertilization or implantation, which was further documented by histological section of the uteri of the rabbit. Histological examination of the tissue biopsy did not reveal any pathological or toxic reactions in any of the organs.

Five months after the last immunization, the anti-receptor antibody titer declined to significantly low levels, the anti-receptor antisera also showed binding to $^{125}I$-hCG. At that time, a repeat induction of ovulation and artificial insemination was followed by another laparotomy in rabbit A (see FIG. 2). The ovaries in rabbit A were found to be of normal size with many follicles, but there was no sign of ovulation or fertilization. Uteri were of normal size and appearance. To rule out the possibility of the endogenous idiotypic antibodies against hCG as the cause of ovulation failure in rabbit A, two weeks later rabbit A was mated and another laparotomy was performed 24 hours later. Both of the ovaries showed many follicles; the right ovary had one antrum follicle and the left ovary had four antrum follicles (see FIG. 2). There was, however, no sign of ovulation indicating that endogenous LH surge in response to mating was also neutralized by endogenous idiotypic anti-antibodies against hCG.

Figure 3:
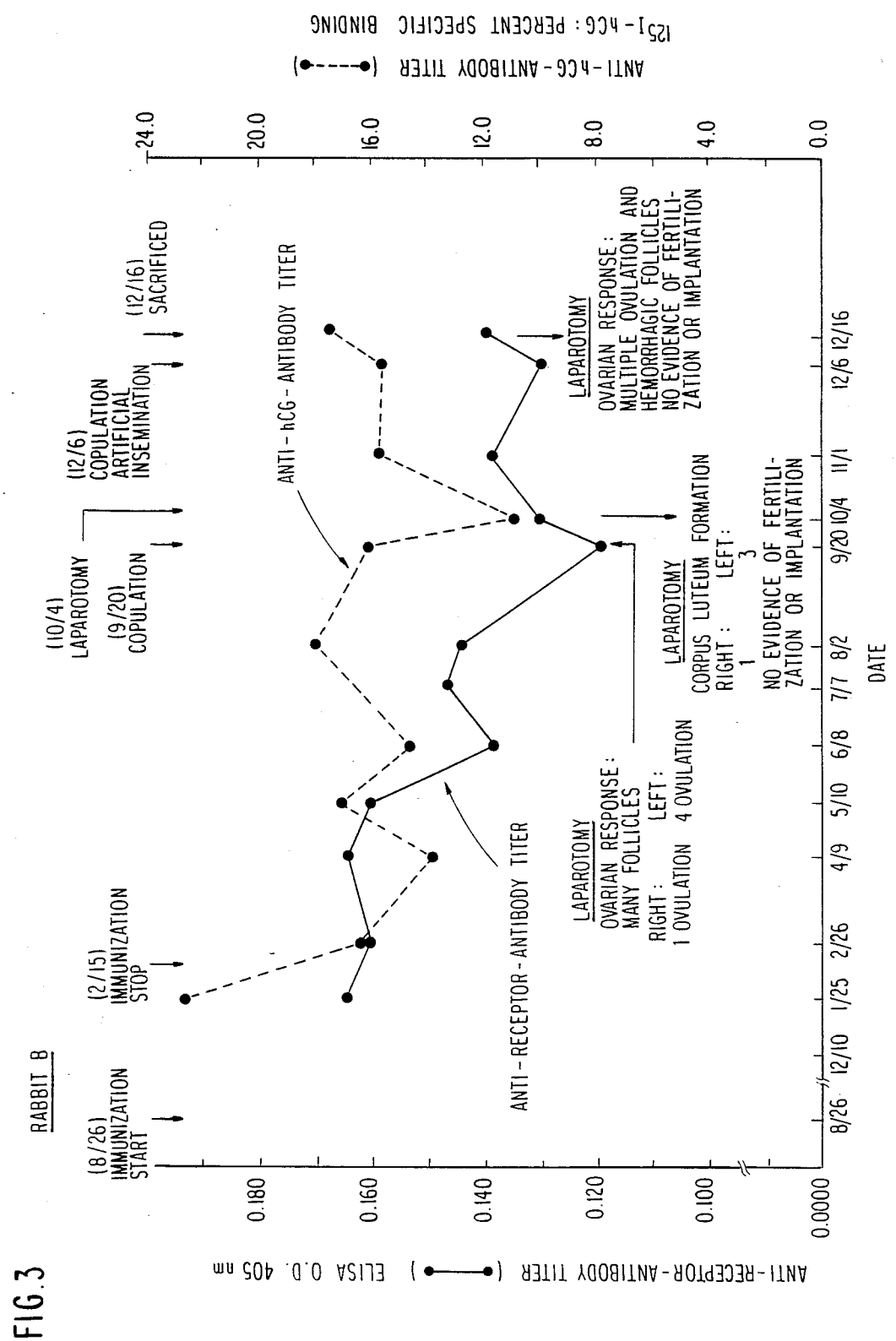

Two weeks later, both rabbits A and B were mated again and 24 hours later laparotomy was performed. In rabbit A there were many follicles but four antrum follicles on left ovary and one antrum follicle in the right ovary but again there was no ovulation on both ovaries (see FIG. 2). In rabbit B, however, laparotomy revealed four sites of ovulation in the left ovary and one site of ovulation in the right ovary and many antrum follicles but again there was no ovulation on both ovaries (see FIG. 3). Uteri and ovaries appeared normal in rabbit B. Thirteen days later another laparotomy was performed in rabbit B. As shown in FIG. 3, the left ovary showed three *Corpora lutea*; There was no evidence of -fertilization or implantation in any of the rabbits in the presence of the antibody.

Hormonal analysis performed on the sera of rabbits A, B and C prior to immunization and on various days during immunization indicated that the Estradiol levels ranged from 40 to 90 pg/ml in the immunized rabbits, as compared to an average of 80 pg/ml in pooled serum of non-immunized rabbits A, B and C. The LH levels were <2.5 mg/ml and were significantly lower than 14.0 ng/ml of the pooled serum of non-immunized rabbits. The lower levels of LH may be due to its neutralization by idiotypic antibody. The progesterone levels ranged from 0 to 1.6 ng/ml and were also significantly lower than 4.7 ng/ml, of the pooled serum of non-immunized rabbits. The hormonal levels and the reproductive function returned to normal with the disappearance of the antibody from the blood.

The above-described studies demonstrate that active immunization against the receptor provides an effective, safe and reversible interruption of fertility.

EXAMPLE 2

Passive Immunization in Rats

A total of 12 (6 female and 6 male) Sprague-Dawley rats, 55-75 days old were boarded in an animal facility. The female rats were divided into two groups namely an experimental group and a control group. The gamma-globulin fraction was isolated by Rivanol precipitation, as described above from the serum of rabbits immunized against receptor prepared as described in Reference Example 2 for six months. The gamma-globulin fraction was evaluated in biological as well as in immunological in vitro assays for (1) inhibition of the production of testosterone by rat Leydig cells to the stimulation of hCG, (2) inhibition of specific binding of hCG to membrane receptor of bovine *Corpora lutea* and (3) inhibition of binding of hCG to rat Leydig cells in the presence of the immuno-gamma-globulin as described in Example 1 above. Intraperitoneal or intramuscular injections of immuno-gamma-globulin were given to the experimental groups of rats. The control group received the same dose of gamma-globulin isolated from normal rat serum. Changes in the estrus cycle were used as an indicator of the specific effect of the passive immunization by immuno-gamma-globulin containing receptor antibody. The estrus cycle was evaluated from the vaginal smears obtained twice a day at 9 a.m. and 9 p.m. and examined under a phase contrast microscope by counting the cornified cells, leukocytes and nucleated epithetical cells. The experimental groups showed the antibody titer in the circulation and their estrus cycle was distributed in contrast with a control group. The effects of passive immunization against the receptor antibody demonstrated that disturbances of the estrus cycle of rats occurred and that these disturbances were the result of passive immunization of the rats by the gamma-globulin isolated from receptor rabbit antiserum.

EXAMPLE 3

Active Immunization in Baboons

Figure 4:
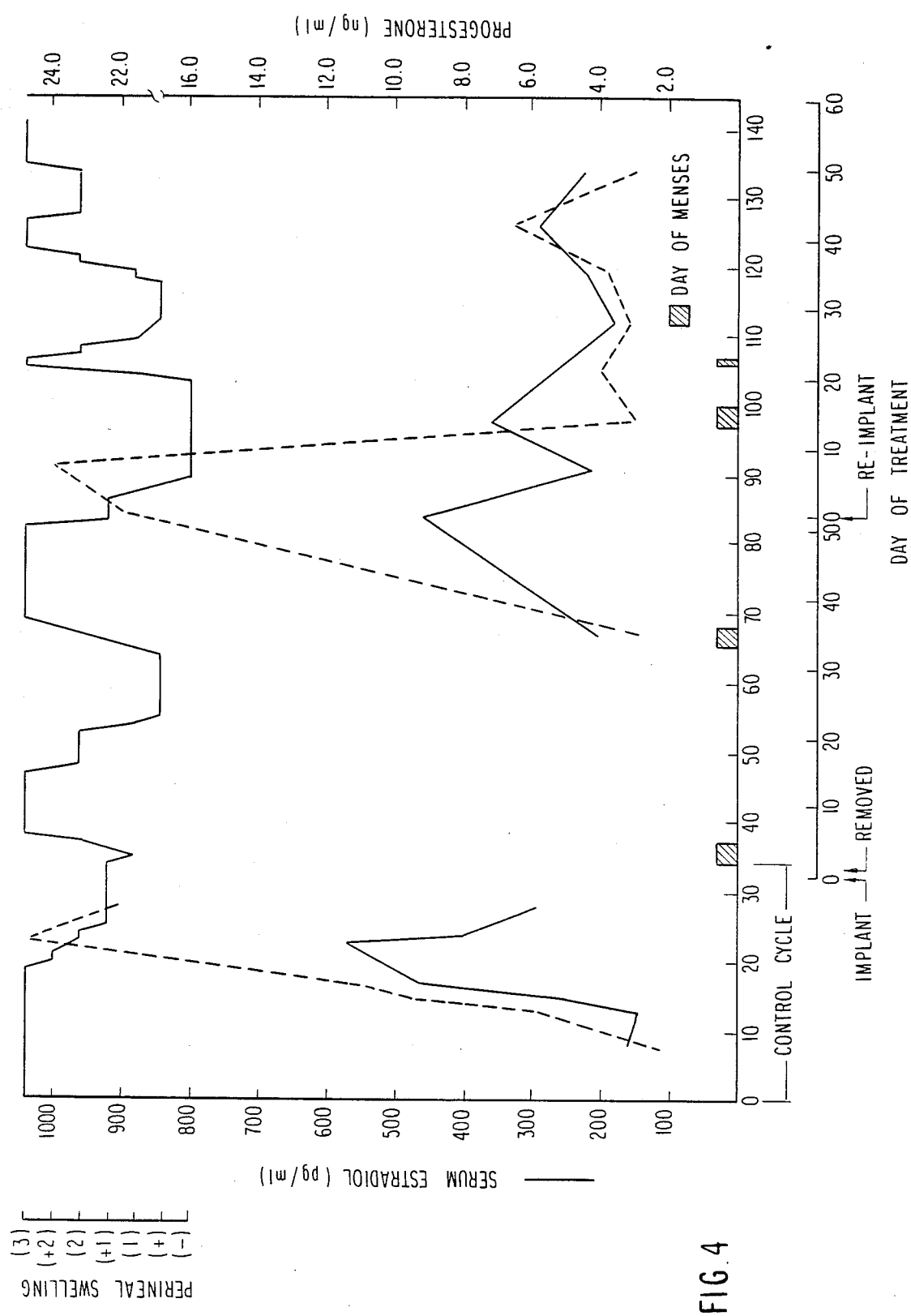
FIGS. 4–6 graphically illustrate the effect of endogenous anti-receptor antibody on reproductive functions in female baboons.
Figure 5:
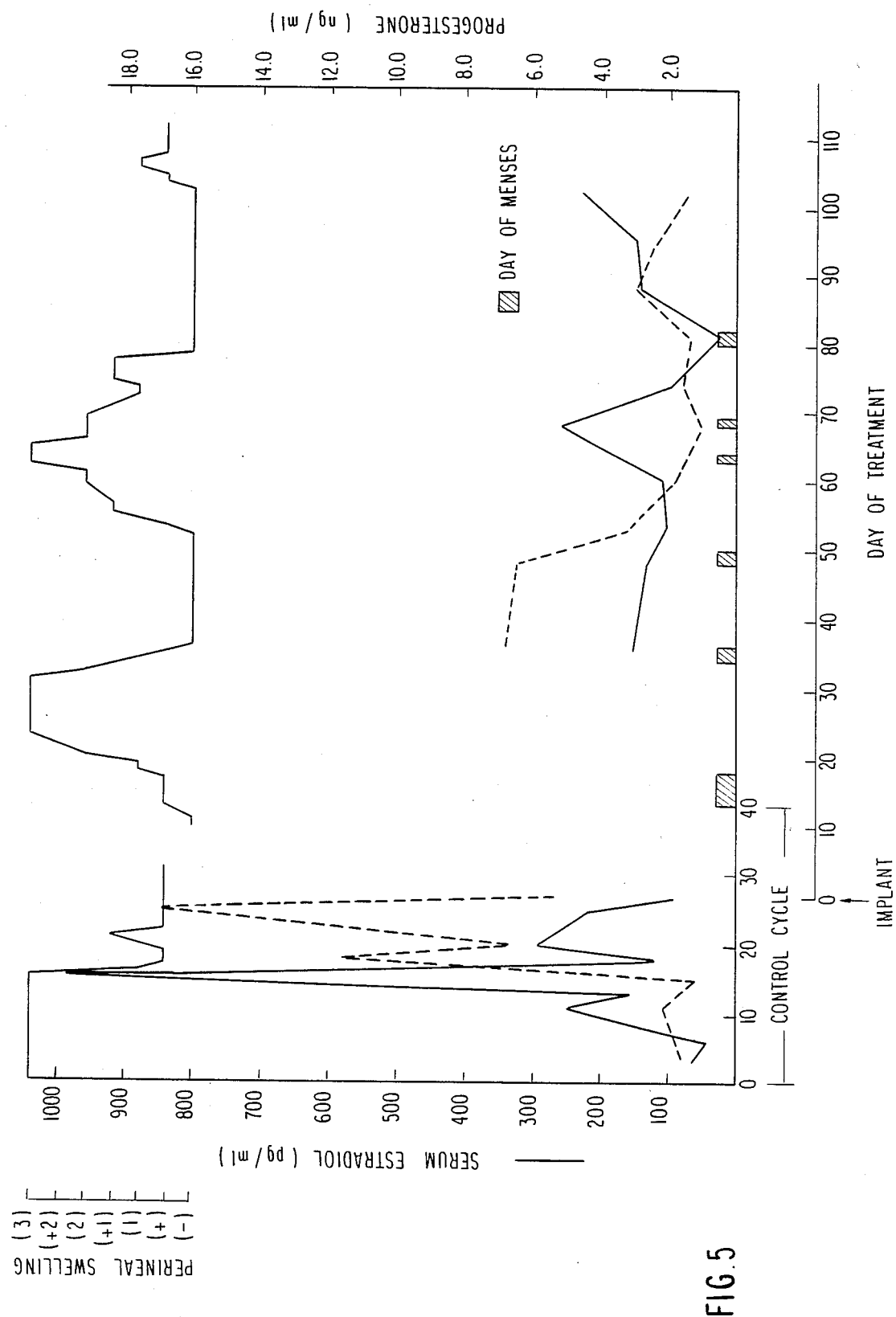
Figure 6:
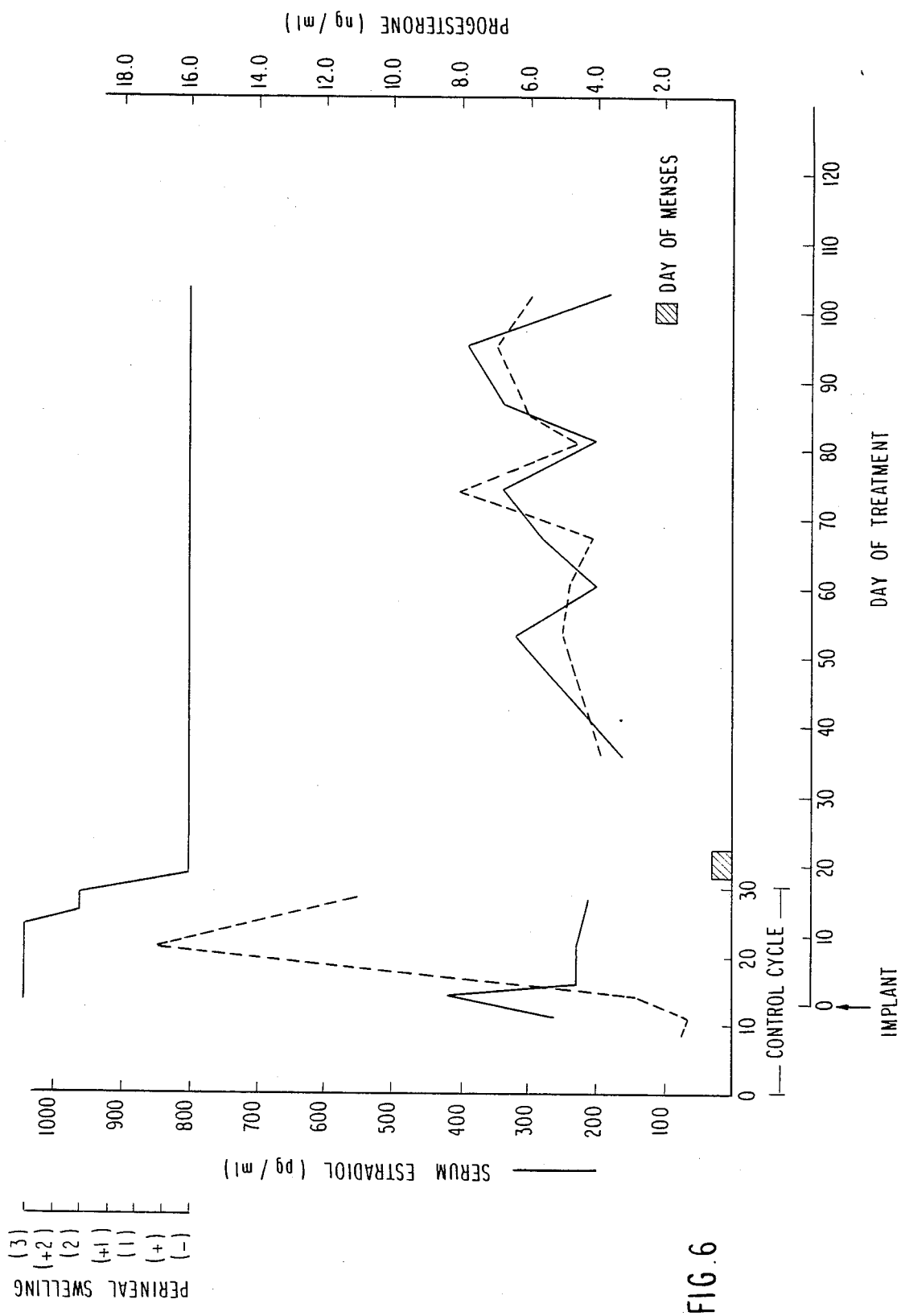

Highly purified LH-hCG receptor was prepared as described in Reference Example 2. Three adult female normally cycling baboons (Papio) were immunized against the receptor using silastic implants prepared as described above. Prior to implantation, the baboons showed normal serum chemistry profile and low density lipoprotein: high density lipoprotein ratio as well as cyclic changes in the serum levels of FSH, LH. $E_2$ and P as determined by radioimmunoassay. Each of the baboons received one implant. Antibody against the receptor was detected in the blood sample at 3-4 weeks after the implantation. One baboon removed the implant and continued to have normal menstrual cycle with cyclic changes in perineal swelling and ovulatory pattern of $E_2$ and P secretion. Hence the receptor was reimplanted (see FIG. 4). A second baboon, who had been implanted during the luteal phase, had normal menstruation but subsequently had polymenorrhea and partial regression of perineal swelling (see FIG. 5). A third baboon who had been implanted at midcycle subsequently showed luteal phase with total regression of perineal swelling and amenorrhea. During the post implant period there was suppression of midcycle $E_2$ and P surge. The antibody titer rose gradually and reached maximum levels (see FIG. 6). From one of the baboons, who was amenorrheic with no changes in perineal swelling, the implant was removed after approximately 200 days to observe the reversibility of the state of infertility. Two weeks after removal of the implant, when the serum levels of the antibody titers were also in the declining phase, midcycle and luteal phase serum levels of $E_2$ and P rose with typical cyclic changes in the perineal skin indicative of the ovulatory cycle, and were removed by normal menstrual bleeding. The implants were removed from the other two baboons between 200 and 220 days and these baboons were found to return to fertility. All of the baboons showed no toxic or adverse effects and returned to normal reproductive function and hormonal profile concomitant with the disappearance of the antibody from the blood.

The above-described studies demonstrate that active immunization against the receptor is safe, reversible and a long term contraceptive vaccine.

While this invention has been described in detail and with reference to specific embodiments thereof, it will be apparent to one skilled in the art that various changes and modifications could be made therein without departing from the spirit and scope thereof.

We claim:

1. An antigen capable of being administered to a host animal to selectively induce an antibody response comprising:
   (A) a first unit selected from the group consisting of
      (i) human chorionic gonadotropin, and (ii) a β-subunit of human chorionic gonadotropin, and (B) a second unit comprising a purified receptor for human chorionic gonadotropin conjugated with said first unit, said antigen being capable of selectively inducing an antibody response to each of said first unit and second unit thereof.

2. The antigen of claim 1 wherein the antigen comprises the β-subunit of human chorionic gonadotropin.

3. The antigen of claim 2 wherein the second unit of the antigen comprises a purified fraction of an extract containing the naturally-occurring receptor for human chorionic gonadotropin.

4. The antigen of claim 3 wherein the extract is of a plasma membrane of a corpus luteum of a species containing the receptor for human chorionic gonadotropin.

5. The antigen of claim 1 or claim 4 wherein the second unit is a substantially pure glycoprotein obtained from a naturally-occurring source of the common receptor for hLH and hCG and having the following characteristics:
   (a) being electrophoretically homogeneous;
   (b) a molecular weight of the aggregate of about 5.9 million ±10%: and
   (c) having specific binding capability for hLH and hCG.

6. The antigen of claim 5 wherein the glycoprotein has a specific binding capacity of at least 2,000 pM hCG/mg protein.

7. The antigen of claim 5 wherein the glycoprotein has the following additional characteristics:
   (a) an amino acid analysis (percent by weight ±10% as follows:

| | | |
|---|---|---|
| ASPARTIC ACID | 9.1 | |
| THREONINE | 5.3 | |
| SERINE | 5.8 | |
| GLUTAMIC ACID | 12.1 | |
| PROLINE | 5.2 | |
| GLYCINE | 4.5 | |
| ALANINE | 4.8 | |
| VALINE | 8.3 | |
| Cysteic Acid | 2.4 | as determined by performic acid oxidation on a separate aliquot |
| METHIONINE | 2.3 | |
| ISOLEUCINE | 4.4 | |
| LEUCINE | 8.7 | |
| TYROSINE | 4.9 | |
| PHENYLALANINE | 5.0 | |
| LYSINE | 7.0 | |
| HISTIDINE | 2.8 | |
| ARGININE | 7.4 | |
| | 100.0 | |

(b) a carbohydrate composition comprising mannose, galactose, N-acetylglucosamine N-acetylgalactosamine and sialic acid.

8. The antigen of claims 1 or 4 wherein the second unit is a substantially pure glycoprotein obtained from a naturally-occurring source of the common receptor for hLH and hCG having the following characteristics:
   (a) being electrophoretically homogeneous;
   (b) a molecular weight of about 240,000 to 280,000±10%: and
   (c) having specific binding capability for hLH and hCG.

9. The antigen of claims 1 or 4 wherein the second unit is a substantially pure glycoprotein obtained from a naturally-occurring source of the common receptor for hLH and hCG having the following characteristics:
   (a) being electrophoretically homogeneous;
   (b) a molecular weight of about 120,000 to 140,000±10%: and
   (c) having specific binding capability for hLH and hCG.

10. The antigen of claims 1 or 4 wherein the second unit is a substantially pure glycoprotein obtained from a naturally-occurring source of the common receptor for hLH and hCG having the following characteristics:
    (a) being electrophoretically homogeneous;
    (b) a molecular weight of about 34,000 to 38,000±10%; and
    (c) having specific binding capability for hLH and hCG.

11. The antigen of claims 1 or 4 wherein the second unit is a substantially pure glycoprotein obtained from a naturally-occurring source of the common receptor for hLH and hCG having the following characteristics:
    (a) being electrophoretically homogeneous;
    (b) a molecular weight of about 70,000 to 85,000±10%; and
    (c) having specific binding capability for hLH and hCG.

12. A vaccine for preventing pregnancy comprising the antigen of any one of claims 1 through 4 and a pharmaceutically acceptable carrier.

13. A vaccine for preventing pregnancy comprising the antigen of claim 5 and a pharmaceutically acceptable carrier.

14. A vaccine for preventing pregnancy comprising the antigen of claim 6 and a pharmaceutically acceptable carrier.

15. A vaccine for preventing pregnancy comprising the antigen of claim 7 and a pharmaceutically acceptable carrier.

16. A vaccine for preventing pregnancy comprising the antigen of claim 8 and a pharmaceutically acceptable carrier.

17. A vaccine for preventing pregnancy comprising the antigen of claim 9 and a pharmaceutically acceptable carrier.

18. A vaccine for preventing pregnancy comprising the antigen of claim 10 and a pharmaceutically acceptable carrier.

19. A vaccine for preventing pregnancy comprising the antigen of claim 11 and a pharmaceutically acceptable carrier.

20. A vaccine for preventing pregnancy comprising in combination in an amount sufficient for preventing pregnancy (1) human chorionic gonadotropin or the β-subunit of human chorionic gonadotropin as an antigen capable of selectively generating antibodies comprising determinants for human chorionic gonadotropin, and (2) a purified receptor for human chorionic gonadotropin as an antigen capable of selectively generating antibodies comprising determinants for the naturally-occurring receptor for human chorionic gonadotropin, and a pharmaceutically acceptable carrier.

21. A method for preventing pregnancy comprising administering to a female the vaccine of claim 20 in an amount effective for preventing pregnancy.

22. A vaccine for preventing pregnancy comprising in an amount effective for preventing pregnancy a purified naturally-occurring receptor for human chorionic gonadotropin as an antigen capable of selectively generating antibodies comprising determinants for the naturally-occurring receptor for human chorionic gonadotropin and a pharmaceutically acceptable carrier.

23. The vaccine for preventing pregnancy as claimed in claim 22, wherein said naturally-occurring receptor is prepared by the process comprising the steps of:
   (1) homogenizing a receptor source material in an aqueous medium to disperse the receptor in a liquid aqueous fraction;
   (2) separating membrane-bound protein containing the receptor from the liquid aqueous fraction;
   (3) dispersing the membrane-bound protein in an aqueous medium and extracting the aqueous medium with an organic solvent in which lipids are soluble to remove lipid from the aqueous phase;
   (4) separating the aqueous phase containing the receptor from the remainder of the product of step (3) and concentrating the aqueous phase; and
   (5) fractionating the aqueous phase based upon molecular weight to remove inert proteins and concentrating the receptor fraction.

24. The vaccine for preventing pregnancy as claimed in claim 23, wherein the process further comprises the steps of:
   (6) subjecting the receptor fraction to electrophoresis to separate said fraction from other remaining protein fractions; and
   (7) purifying the receptor fraction by subjecting it to immuno affinity chromatography.

25. The vaccine for preventing pregnancy of claims 22, 23, or 24 wherein the receptor for hCG is a glycoprotein having the following characteristics:
   (a) being electrophoretically homogeneous;
   (b) a molecular weight of the aggregate of about 5.9 million ±10%; and
   (c) having specific binding capability for hLH and hCG.

26. The vaccine for preventing pregnancy as claimed in claim 25 wherein the glycoprotein has a specific binding capacity of at least 2,000 pM hCG/mg protein.

27. The vaccine for preventing pregnancy as claimed in claim 25 wherein the glycoprotein has the following additional characteristics:
   (a) an amino acid analysis (percent by weight±10%) as follows:

| ASPARTIC ACID | 9.1 |
| --- | --- |
| THREONINE | 5.3 |
| SERINE | 5.8 |
| GLUTAMIC ACID | 12.1 |
| PROLINE | 5.2 |
| GLYCINE | 4.5 |
| ALANINE | 4.8 |
| VALINE | 8.3 |
| Cysteic Acid | 2.4 | as determined by performic acid oxidation on a separate aliquot |
| METHIONINE | 2.3 |
| ISOLEUCINE | 4.4 |
| LEUCINE | 8.7 |
| TYROSINE | 4.9 |
| PHENYLALANINE | 5.0 |
| LYSINE | 7.0 |
| HISTIDINE | 2.8 |
| ARGININE | 7.4 |
| | 100.0 |

(b) a carbohydrate composition comprising mannose, galactose, N-acetylglucosamine, N-acetylgalactosamine and sialic acid.

28. The vaccine for preventing pregnancy as claimed in claims 22, 23 or 24 wherein the receptor for hCG is a glycoprotein having the following characteristics:
   (a) being electrophoretically homogeneous;
   (b) a molecular weight of about 240,000 to 280,000±10%; and
   (c) having specific binding capability for hLH and hCG.

29. The vaccine for preventing pregnancy as claimed in claims 22, 23 or 24 wherein the receptor for hCG is a glycoprotein having the following characteristics:
   (a) being electrophoretically homogeneous;
   (b) a molecular weight of about 120,000 to 140,000±10%: and
   (c) having specific binding capability for hLH and hCG.

30. The vaccine for preventing pregnancy as claimed in claims 22, 23 or 24 wherein the receptor for hCG is a glycoprotein having the following characteristics:
   (a) being electrophoretically homogeneous;
   (b) a molecular weight of about 34,000 to 38.000±10%; and
   (c) having specific binding capability for hLH and hCG.

31. The vaccine for preventing pregnancy as claimed in claims 22, 23 or 24 wherein the receptor for hCG is a glycoprotein having the following characteristics:
   (a) being electrophoretically homogeneous;
   (b) a molecular weight of about 70,000 to 85,000±10%; and
   (c) having specific binding capability for hLH and hCG.

32. A process for preventing pregnancy comprising administering to a female the vaccine of any one of claims 22–24 in an amount sufficient for preventing pregnancy.

* * * * *